（12） United States Patent
Yeh et al.

(10) Patent No.: US 11,964,214 B2
(45) Date of Patent: Apr. 23, 2024

(54) SYSTEMS AND METHODS FOR ADJUSTING AN OPERATION OF AN ATTRACTION SYSTEM

(71) Applicant: Universal City Studios LLC, Universal City, CA (US)

(72) Inventors: Wei Cheng Yeh, Orlando, FL (US); Rachel Elise Rodgers, Orlando, FL (US)

(73) Assignee: UNIVERSAL CITY STUDIOS LLC, Universal City, CA (US)

( * ) Notice: Subject to any disclaimer, the term of this patent is extended or adjusted under 35 U.S.C. 154(b) by 260 days.

(21) Appl. No.: 17/357,669

(22) Filed: Jun. 24, 2021

(65) Prior Publication Data
US 2022/0054948 A1 Feb. 24, 2022

Related U.S. Application Data

(60) Provisional application No. 63/067,700, filed on Aug. 19, 2020.

(51) Int. Cl.
A63G 31/00 (2006.01)
A61B 5/0205 (2006.01)
A61B 5/024 (2006.01)
A61B 5/0507 (2021.01)
A61B 5/08 (2006.01)
G16H 40/63 (2018.01)
A63G 7/00 (2006.01)
A63J 5/02 (2006.01)

(52) U.S. Cl.
CPC .......... *A63G 31/00* (2013.01); *A61B 5/0205* (2013.01); *A61B 5/024* (2013.01); *A61B 5/0507* (2013.01); *A61B 5/0816* (2013.01); *G16H 40/63* (2018.01); *A63G 7/00* (2013.01); *A63J 5/02* (2013.01)

(58) Field of Classification Search
CPC ........ G06Q 10/00; A63G 31/00; A63G 31/12; A63G 31/16; A63G 7/00
USPC ........................................ 472/59–61, 13, 43
See application file for complete search history.

(56) References Cited

U.S. PATENT DOCUMENTS 7,908,237 B2    3/2011  Angell et al.
9,381,916 B1    7/2016  Zhu et al.
10,528,123 B2   1/2020  McCracken et al.
10,576,328 B2 * 3/2020  Santra ..................... G01S 13/42
(Continued)

OTHER PUBLICATIONS

Yu-Wen Chang, Michael Johnson, Portable Concealed Weapon Detection Using Millimeter Wave FMCW Radar Imaging, National Criminal Justice Reference Service, Aug. 30, 2001, 30 Pages.
(Continued)

Primary Examiner — Kien T Nguyen
(74) Attorney, Agent, or Firm — Fletcher Yoder, PC

(57) ABSTRACT

An attraction system for entertaining guests includes a millimeter wave (mmWave) sensor configured to transmit a signal within the attraction system and to receive a reflection of the signal and a control system communicatively coupled to the mmWave sensor. The mmWave sensor is configured to transmit data to the control system based on the reflection of the signal, and the control system is configured to perform operations that include determining a target operation of the attraction system based on the data received from the mmWave sensor and operating the attraction system based on the target operation.

20 Claims, 4 Drawing Sheets

(56) References Cited

U.S. PATENT DOCUMENTS

| | | |
|---|---|---|
| 2009/0234666 A1 | 9/2009 | Crawford et al. |
| 2019/0011534 A1* | 1/2019 | Trotta .................... G06F 21/32 |
| 2020/0098182 A1 | 3/2020 | Melo et al. |
| 2020/0258281 A1 | 8/2020 | Churchill et al. |

OTHER PUBLICATIONS

Dan Wang, Cascaded Radar and Body&Chassis Automotive Applications, Texas Instruments, Sep. 12, 2018, 71 Pages.

Douglas T. Petkie, Erik Bryan, Carla Benton, Brian D. Rigling, Millimeter-wave radar systems for biometric applications, Proceedings of SPIE vol. 7485, Sep. 2009, 8 Pages, https://www.researchgate.net/publication/241196561_Millimeter-wave_radar_systems_for_biometric_applications.

Feng Jin, Rengyuan Zhang, Arindam Sengupta, Siyang Cao, Salim Hariri, Nimit K. Agarwal, Sumit K. Agarwal, Multiple Patients Behavior Detection in Real-time using mmWave Radar and Deep CNNs, Feb. 12, 2019, 7 Pages, https://www.researchgate.net/publication/331048505_Multiple_Patients_Behavior_Detection_in_Real-time_using_mmWave_Radar_and_Deep_CNNs.

PCT/US2021/045172 International Search Report and Written Opinion dated Nov. 18, 2021.

\* cited by examiner

SYSTEMS AND METHODS FOR ADJUSTING AN OPERATION OF AN ATTRACTION SYSTEM

CROSS REFERENCE TO RELATED APPLICATIONS

This application claims priority from and the benefit of U.S. Provisional Application Ser. No. 63/067,700, entitled "SYSTEMS AND METHODS FOR ADJUSTING AN OPERATION OF AN ATTRACTION SYSTEM," filed Aug. 19, 2020, which is hereby incorporated by reference in its entirety for all purposes.

BACKGROUND

This section is intended to introduce the reader to various aspects of art that may be related to various aspects of the present disclosure. This discussion is believed to be helpful in providing the reader with background information to facilitate a better understanding of the various aspects of the present disclosure. Accordingly, it should be noted that these statements are to be read in this light and not as admissions of prior art.

Amusement parks typically include various attractions that provide unique experiences for guests. For example, an amusement park may include various rides and show performances. As technology has continued to improve, such attractions have increased in sophistication and complexity. There is a corresponding increase in expectations regarding entertainment quality of attractions. As a result, improved and more creative attractions are needed.

BRIEF DESCRIPTION

A summary of certain embodiments disclosed herein is set forth below. It should be noted that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, an attraction system for entertaining guests includes a millimeter wave (mmWave) sensor configured to transmit a signal within the attraction system and to receive a reflection of the signal and a control system communicatively coupled to the mmWave sensor. The mmWave sensor is configured to transmit data to the control system based on the reflection of the signal, and the control system is configured to perform operations that include determining a target operation of the attraction system based on the data received from the mmWave sensor and operating the attraction system based on the target operation.

In an embodiment, a tangible, non-transitory, computer-readable medium comprising executable instructions that, when executed by processing circuitry, are configured to cause the processing circuitry to perform operations for an attraction system. The operations include receiving data from a millimeter wave (mmWave) sensor, in which the data is indicative of a parameter associated with the attraction system, determining a target operation of the attraction system based on the data received from the mmWave sensor, and operating the attraction system based on the target operation.

In an embodiment, an attraction system for entertaining a guest includes a first millimeter wave (mmWave) sensor configured to transmit a first signal within the attraction system and to receive a reflection of the first signal, a second mmWave sensor configured to transmit a second signal within the attraction system and to receive a reflection of the second signal, and a control system communicatively coupled to the first mmWave sensor and to the second mmWave sensor. The first mmWave sensor is configured to transmit first data to the control system based on the reflection of the first signal, the second mmWave sensor is configured to transmit second data based on the reflection of the second signal, and the control system is configured to perform operations the include determining a target operation of the attraction system based on the first data, the second data, or both, and operating the attraction system based on the target operation.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
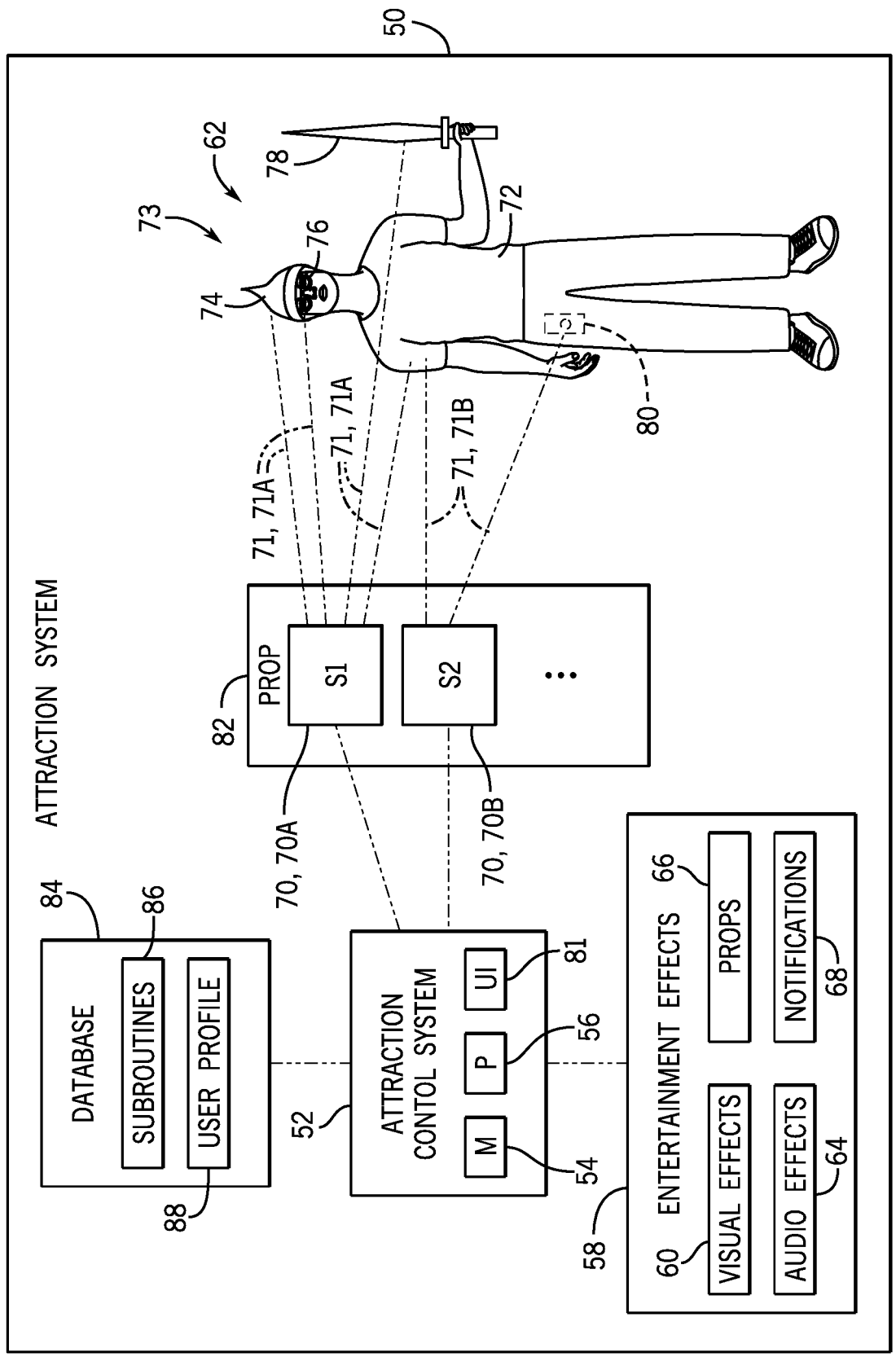
FIG. 1 is a schematic diagram of an embodiment of an attraction system having an adjustment control system configured to operate the attraction system based on data transmitted by a millimeter wave (mmWave) sensor, in accordance with an aspect of the present disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. One or more specific embodiments of the present embodiments described herein will be described below. In an effort to provide a concise description of these embodiments, all features of an actual implementation may not be described in the specification. It should be noted that in the development of any such actual implementation, as in any engineering or design project, numerous implementation-specific decisions must be made to achieve the developers' specific goals, such as compliance with system-related and business-related constraints, which may vary from one implementation to another. Moreover, it should be noted that such a development effort might be complex and time consuming, but would nevertheless be a routine undertaking of design, fabrication, and manufacture for those of ordinary skill having the benefit of this disclosure.

The present disclosure is related to an attraction system, such as an attraction system for an amusement park. The attraction system may include a control system configured to detect certain parameters associated with the attraction system and to operate the attraction system based on such parameters. As an example, the control system may adjust operations to provide a more unique or personalized experience for a guest of the amusement park. For instance, the attraction system may use a sensor configured to monitor data indicative of a reaction of a guest, a physical profile of a guest, an accessory of a guest, and the like. The control system may receive the data from the sensor and may adjust the operations of certain entertainment aspects based on the data, such as by changing an operation of visual effects, audio effects, and/or other features presented to the guest. Furthermore, the control system may associate certain operations and/or operational settings of the attraction system with a specific guest for use at a later time. For example, the control system may store a user profile associating a particular operation of the attraction system with stored data associated with a guest and, upon determination that detected data matches the stored data associated with the user profile (e.g., to indicate detection of the guest in the attraction system), the control system may reference the user profile to operate the attraction system in accordance with the corresponding operation associated with the user profile.

In particular, the attraction system may employ a millimeter wave (mmWave) sensor (e.g., a mmWave radar) to gather data. As used herein, a mmWave sensor continuously transmits a signal having a millimeter (mm) wavelength. The signals may reflect off an object to return to the mmWave sensor. The mmWave sensor then determines a characteristic, such as an amplitude, a return time, and so forth, of each signal returning to and received by the mmWave sensor. The mmWave sensor may determine a parameter of the object, such as a position of the object within the attraction system, a texture of the object, a size of the object, a speed of the object, and the like, based on the characteristic of the return signals, and the mmWave sensor may transmit data that includes the parameter to the control system. The control system may therefore adjust operation of the attraction system based on the parameter indicated by the data. The signal transmitted by the mmWave sensor may penetrate certain materials based on its wavelength and/or frequency. For this reason, the mmWave sensor may be embedded or hidden within an object, such as a prop of the attraction system, and may not be visible to the guest, thereby increasing an immersive experience provided to the guest. In one embodiment, the attraction system may implement a mmWave sensor configured to emit a signal having a specific wavelength and/or frequency to enable the signal to have a particular depth of penetration and enable the mmWave sensor to detect a parameter of a specific object (e.g., an exposed object, a hidden object). As an example, the mmWave sensor may emit a signal that may penetrate certain clothing material (e.g., fabric) so as to detect skin texture of a guest, additional accessories (e.g., a bracelet) worn by the a guest, and so forth. As another example, the mmWave sensor may emit a signal that does not penetrate clothing material so as to detect the particular clothing worn by the guest. Indeed, multiple mmWave sensors, each configured to transmit a respective signal having a different wavelength and/or frequency, may be employed to detect parameters of multiple different objects to facilitate adjusting operation of the attraction system via the control system.

With the preceding in mind, FIG. 1 is a schematic diagram of an embodiment of an attraction system 50, which may be a part of an amusement park. For instance, the attraction system 50 may include a roller coaster, an interactive game, a theatric show, another suitable type of attraction system, or any combination thereof. The attraction system 50 may include an attraction control system 52 (e.g., an electronic controller) configured to control operations of certain features of the attraction system 50. To this end, the attraction control system 52 may include a memory 54 and processing circuitry 56, such as a microprocessor. The memory 54 may include one or more of a volatile memory, such as random access memory (RAM), and/or non-volatile memory, such as read-only memory (ROM), optical drives, hard disc drives, solid-state drives, or any other tangible, non-transitory, computer-readable medium that includes executable instructions to operate the attraction system 50. The processing circuitry 56 may include one or more application specific integrated circuits (ASICs), one or more field programmable gate arrays (FPGAs), or any combination thereof, configured to execute the instructions stored in the memory 54.

For example, the attraction control system 52 may control operation of various entertainment effects 58 of the attraction system 50. The entertainment effects 58 may include visual effects, such as lighting, projections, images, and so forth, presented to a guest 62. The entertainment effects 58 may additionally or alternatively include audio effects 64, such as sounds, presented to the guest 62. The entertainment effects 58 may also include operation of certain props 66. As an example, the attraction control system 52 may control movement of certain electromechanical figures (e.g., robots), positioning of certain objects, and the like. As another example, the prop 66 may include an interactive feature with which the guest 62 may interact. For instance, the prop 66 may include a microphone or an audio sensor, and the attraction control system 52 may adjust a functionality of the microphone or audio sensor based on the data (e.g., data associated with the voice of the guest 62), such as by changing a volume of audio playback. In this manner, the attraction control system 52 may adjust an interactive experience of the guest 62.

The attraction control system 52 may further control sending of certain notifications 68. For instance, in an embodiment, the attraction system 50 may send notifications 68 to the guest 62 (e.g., to a mobile device of the guest 62) to provide supplemental information associated with the attraction system 50, such as to provide a narration that aligns with the operation of the attraction system 50. The notifications 68 may provide the guest 62 with a method to interact with the attraction system 50 and/or to guide the guest 62 through the attraction system 50. Additionally or alternatively, the attraction control system 52 may send such notifications 68 to a different entity, such as an operator, a worker, and/or a technician of the attraction system 50. By way of example, the notification 68 may urge someone to manually adjust one of the entertainment effects 58, to change a show performance (e.g., to notify a performer to use a new script), or otherwise change the operation of the attraction system 50. In any case, the attraction control system 52 may adjust operations to change the entertainment provided to the guest 62, such as by changing a theme or story, a target level of excitement or other sentiment elicited or induced in the guest 62, and/or another aspect of the attraction control system 52 in order to provide a more unique, personalized, or interactive experience to the guest 62.

Although the present disclosure primarily discusses the attraction control system 52 operating to control the visual effects 60, the audio effects 64, the props 66, and the notification 68 associated with the attraction system 50, an additional or alternative attraction control system 52 may be configured to control another feature of the attraction system 50. For example, the attraction system 50 may include a ride vehicle, and the attraction control system 52 may adjust a path of travel of the ride vehicle (e.g., along a track) based on detected parameters. Indeed, the attraction system 50 may adjust any suitable feature of the attraction system 50 to provide a desirable experience to the guest 62.

The attraction control system 52 may be communicatively coupled to one or more mmWave sensors 70 and may operate based on data received from the mmWave sensor(s) 70. The nmWave sensors 70 may both emit and detect signals. Thus, each nmWave sensor 70 represents at least one emitter and at least one detector. While the nmWave sensors 70 illustrated in FIG. 1 include integral emitters and detectors, in some embodiments, the emitters and detectors may be separate.

The illustrated embodiment includes a first mmWave sensor 70A and a second mmWave sensor 70B, each of which may send respective signals having different wavelengths and/or frequencies to penetrate different materials and to provide readings of various parameters (e.g., associated with the guest 62). For instance, the first mmWave sensor 70A may be configured to transmit a first signal 71A (e.g., having a frequency that is between 60 and 90 gigahertz [GHz]) that does not penetrate through certain materials. By way of example, the first signal 71A may not penetrate through certain objects associated with the guest 62, such as clothing 72 worn by the guest 62, headwear 74 worn by the guest 62, facial accessories (e.g., glasses) 76 associated with the guest 62, an item 78 possessed (e.g., held) by the guest 62, and so forth. In other words, the first signal 71A may reflect off such objects to return to the first mmWave sensor 70A for detection by the first mmWave sensor 70A. Further, the second mmWave sensor 70B may be configured to transmit a second signal 71B (e.g., having a frequency that is between 90 GHz and 300 GHz) that penetrates through objects through which the first signal 71A cannot penetrate. As an example, the second signal 71B may penetrate through the clothing 72 and may reflect off the body of the guest 62, such as off the skin, a temporary tattoo, a sticker, marking, or any other feature that is on or including the skin of the guest 62. The second signal 71B may additionally or alternatively reflect off a hidden object 80 (e.g., disposed within certain clothing 72 of the guest 62, such as within a pocket of the guest 62).

In any case, the mmWave sensors 70 may detect various parameters associated with the guest 62 based on the reflection of the respective signals 71, and the mmWave sensors 70 may transmit data indicative of the parameters to the attraction control system 52. Indeed, the attraction system 50 may include any suitable number of mmWave sensors 70, such as a single mmWave sensor 70, or multiple mmWave sensors 70. For example, the attraction system 50 may use a matrix, a cascade, or an array of mmWave sensors 70 to provide multiple readings of objects at various depths and/or to provide multiple readings of objects at the same depth to facilitate increasing the accuracy of the determined parameters. That is, the matrix of mmWave sensors 70 is configured to detect multiple layers by emitting a cascading of signals. The matrix of mmWave sensors 70 may therefore provide data associated with the layers to the attraction control system 52, and the attraction control system 52 may operate the attraction system 50 based on data received from the matrix of mmWave sensors 70.

In an embodiment, the attraction control system 52 may identify the particular clothing 72 and/or accessories associated with the guest 62 based on the data transmitted by the mmWave sensors 70 (e.g., from the first mmWave sensor 70A). As used herein, the clothing 72 and/or accessories associated with the guest 62 may collectively be referred to as costuming 73. The attraction control system 52 may therefore operate the attraction system 50 to provide entertainment for the guest 62 based on the costuming 73 associated with the guest 62. As an example, the attraction system 50 may include a collection of various costuming 73 from which the guest 62 may select, and the attraction control system 52 may be pre-programmed to operate the attraction system 50 based on identification of any of the costuming 73. That is, the attraction control system 52 may identify the particular costuming 73 selected by the guest 62 based on the data received from the mmWave sensors 70, and the attraction control system 52 may operate based on the identified costuming 73, such as to provide a particularly themed narrative. For instance, in response to identifying the headwear 74 is a sailor's cap, the attraction control system 52 may control the entertainment effects 58 to provide a nautical narrative. In addition, in response to identifying the facial accessories 76 as including sunglasses, the attraction control system 52 may control the entertainment effects 58 to provide a tropical narrative. Further, in response to identifying the item 78 is a sword, the attraction control system 52 may control the entertainment effects 58 to provide a combat-related narrative. Indeed, the attraction control system 52 may control the entertainment effects 58 to operate the attraction system 50 based on any of various costuming 73 (e.g., top, pants, shorts, dress, scarf, facemask, eyepatch, headgear). In this manner, the attraction control system 52 may provide an experience based on a selection made by the guest 62, thereby providing a more customized experience for the guest 62.

The attraction control system 52 may additionally or alternatively provide or enable other aspects of the attraction system 50 based on the identified costuming 73. By way of example, the facial accessory 76 may include a media viewer, such as 3-dimensional glasses and/or an augmented reality headset that can be optionally selectable or wearable by the guest 62. Thus, the attraction control system 52 may receive data indicative of the media viewer and to provide media corresponding to the media viewer. As an example, the attraction control system 52 may provide 3-dimensional images (e.g., offset images that, when viewed through 3-dimensional glasses, generally provide an appearance of depth) and/or augmented reality elements based on the facial accessory 76 worn by the guest 62. For instance, in response to determining that the guest 62 is wearing 3-dimensional glasses instead of an augmented reality device, the attraction control system 52 may present images viewable in 3-dimensions via the 3-dimensional glasses. In response to determining that the guest 62 is wearing an augmented reality device instead of 3-dimensional glasses, the attraction control system 52 may present augmented reality elements (e.g., by sending a signal to the augmented reality device) instead of 3-dimensional images. Further, in response to determining that the guest 62 is not wearing either the 3-dimensional glasses or the augmented reality device, the attraction control system 52 may present 2-dimensional images. Thus, the manner in which the attraction control system 52 presents certain entertainment effects 58 may be based on the type of costuming 73 associated with the guest 62. Further, theming of the facial accessory 76 may be detected and used to guide content provision. For example, a space themed set of 3-dimensional glasses may be detected and the attraction control system may provide 3-dimensional images associated with a space theme.

In an additional or alternative embodiment, the attraction control system 52 may operate the attraction system 50 based on data provided by the second mmWave sensor 70B. In an example, the data associated with the second mmWave sensor 70B may indicate a location and/or an orientation of the guest 62 within the attraction system 50. Indeed, the attraction control system 52 may use data received from a single mmWave sensor 70, cumulative data received from a matrix of mmWave sensors, and/or data received from another sensor (e.g., a location sensor) to perform an operation, such as to present the entertainment effects 58 in a manner that is directed toward the location of the guest 62 within the attraction system 50 (e.g., by activating features that are positioned proximate to the guest 62). In another example, the data may be indicative of a physical profile of the guest 62, such as a height of the guest 62, a texture (e.g., of a feature on or including the guest's skin) associated with the guest 62, a geometry of the guest 62, a vocal cord vibration (e.g., a voice level, pitch) of the guest, a gait or movement of the guest 62, another suitable parameter associated with the guest, or any combination thereof, and the attraction control system 52 may operate the entertainment effects 58 based on the physical profile. In a further example, the data may include biometric data, such as a respiratory rate, a heart rate, a perspiration amount, or other suitable data. Indeed, the data transmitted by the mmWave sensor 70 may indicate motion of a heart (e.g., to indicate a heartbeat), motion of blood vessels, motion of lungs, and/or motion of another body feature. In this way, the data may indicate movement of a feature of the guest 62, and the attraction control system 52 may use such data to derive relevant biometric data. The attraction control system 52 may adjust operation of the attraction system 50 based on the biometric data so as to elicit a desirable response from the guest 62. For instance, the attraction control system 52 may adjust an intensity and/or an excitement of the experience provided by the attraction system 50 based on the biometric data.

Further still, the attraction control system 52 may operate the attraction system 50 based on data indicative of the hidden object 80. For example, the attraction control system 52 may adjust the narrative presented by the attraction system 50 (e.g., by controlling the entertainment effects 58) based on the hidden object 80. In another implementation, attraction control system 52 may send the notification 68 to a worker of the attraction system 50 based on the hidden object 80. For example, the hidden object 80 may include one of the accessories improperly placed within the clothing 72 of the guest 62 (e.g., to indicate attempted theft committed by the guest 62) and/or a unauthorized tool, and the attraction control system 52 may therefore send the notification 68 to inform a worker (e.g., security personnel) to confront the guest 62.

The attraction control system 52 may additionally or alternatively operate the attraction system 50 based on a user input. To this end, the attraction control system 52 may include a user interface 81, which may include a touch screen, a button, a switch, a trackpad, a dial, another suitable feature, or any combination thereof, with which a user (e.g., the guest 62, an operator) may interact to control operation of the attraction system 50. By way of example, the guest 62 may utilize the user interface 81 to transmit a user input indicative of a desirable operational setting and/or experience (e.g., an excitement level) to be provided by the attraction system 50. The attraction control system 52 may therefore operate the attraction system 50 based on the user input received via the user interface 81.

In one embodiment, some of the mmWave sensors 70 may be embedded or hidden within an enclosing prop 82, which may, for example, be one of the props 66. In this manner, the attraction control system 52 may move the enclosing prop 82 to adjust the positioning of the mmWave sensors 70 within the attraction system 50 (e.g., to facilitate capturing data associated with the guest 62). Further, the enclosing prop 82 may hide the mmWave sensors 70 from view from the guest 62, thereby creating a more immersive environment for the guest 62 within the attraction system 50. To this end, the enclosing prop 82 may be made from a certain material, such as plastic, concrete, and/or any suitable non-attenuating material, to enable each of the signals 71 to penetrate through the enclosing prop 82 to reflect off objects within the attraction system 50 and without distorting characteristics of the signals 71. Additionally, the portion of the enclosing prop 82 shielding or covering the mmWave sensors 70 may have a limited thickness, such as less than 1 cm or 0.4 inches, to enable the signals 71 to penetrate through the enclosing prop 82.

In an embodiment, the attraction control system 52 may include and/or be communicatively coupled with a database 84 (e.g., cloud-based storage, physical storage). The database 84 may store certain information that may be retrieved by the attraction control system 52 to facilitate operation of the attraction system 50. As an example, the database 84 may store subroutines 86 or certain operational parameters or settings (e.g., visual effects 60 to be presented, audio effects 64 to be presented, movement control of the props 66, notifications 68 to be sent) in which the attraction control system 52 may operate the attraction system 50. Each of the subroutines 86 may be associated with a particular parameter identifiable by the attraction control system 52. Accordingly, in response to identifying a parameter (e.g., based on the data transmitted by the mmWave sensors 70), the attraction control system 52 may select the associated subroutine from the stored subroutines 86 to operate the attraction system 50. For instance, the attraction control system 52 may operate the attraction system 50 based on a first subroutine in response to identifying the headwear 74 as a first headwear, and the attraction control system 52 may operate a second subroutine in response to identifying the headwear 74 as a second headwear. The attraction control system 52 may also operate the attraction system 50 based on a third subroutine in response to identifying the guest 62 also possesses a particular item 78. Additionally or alternatively, the guest 62 may utilize the user interface 81 to directly indicate a desired set of subroutines 86 to be effectuated by the attraction control system 52. In any case, the attraction control system 52 may operate the attraction system 50 based on a combination of subroutines 86, thereby operating the attraction system 50 in different manners to provide a diverse experience for the guest 62.

In an additional or alternative embodiment, the database 84 may store a user profile 88 associated with the guest 62. The user profile 88 may be associated with certain operations, such as a specific set of subroutines 86, to be effectuated by the attraction control system 52 (e.g., based on a previous experience undergone by the guest 62 in the attraction system 50). The user profile 88 may further be associated with certain parameters detected by the mmWave sensors 70 and indicative of the specific guest 62. For example, during a first operation of the attraction system 50, the attraction control system 52 may receive data from the mmWave sensors 70 and/or a user input from the user interface 81 to cause the attraction control system 52 to operate the attraction system 50 in accordance with a first set of subroutines, and the attraction control system 52 may also store the user profile 88 associated with the guest 62, including the data received from the mmWave sensors 70 (e.g., indicative of a physical profile of the guest 62) and the first set of subroutines 86 associated with the guest 62, within the database 84.

During a second operation of the attraction system 50, the attraction control system 52 may receive additional data from the mmWave sensors 70 and compare the additional data with the data associated with the user profile 88 stored in the database 84. In response to determining the additional data received from the mmWave sensors 70 matches with the data associated with the user profile 88, the attraction control system 52 may automatically operate the attraction system 50 in accordance with the first set of subroutines 86 associated with the user profile 88, such as if the guest 62 appeared to be satisfied with the experience provided by the first operation of the attraction system 50. As an example, the attraction control system 52 may prompt the guest 62 to indicate whether operation of the attraction system 50 in accordance to the first set of subroutines 86 again is desirable, and the guest 62 may confirm that the attraction control system 52 is to operate the attraction system in accordance with the first set of subroutines 86 during the second operation of the attraction system 50. Additionally or alternatively, the attraction control system 52 may operate the attraction system 50 in accordance with a second set of subroutines 86 to provide a different experience for the guest 62, such as based on a user input indicative that the guest 62 desires a different experience to be provided by the attraction system 50 during the second operation of the attraction system 50. As such, the attraction control system 52 may provide a more personalized experience each time the guest 62 goes through the attraction system 50.

Figure 2:
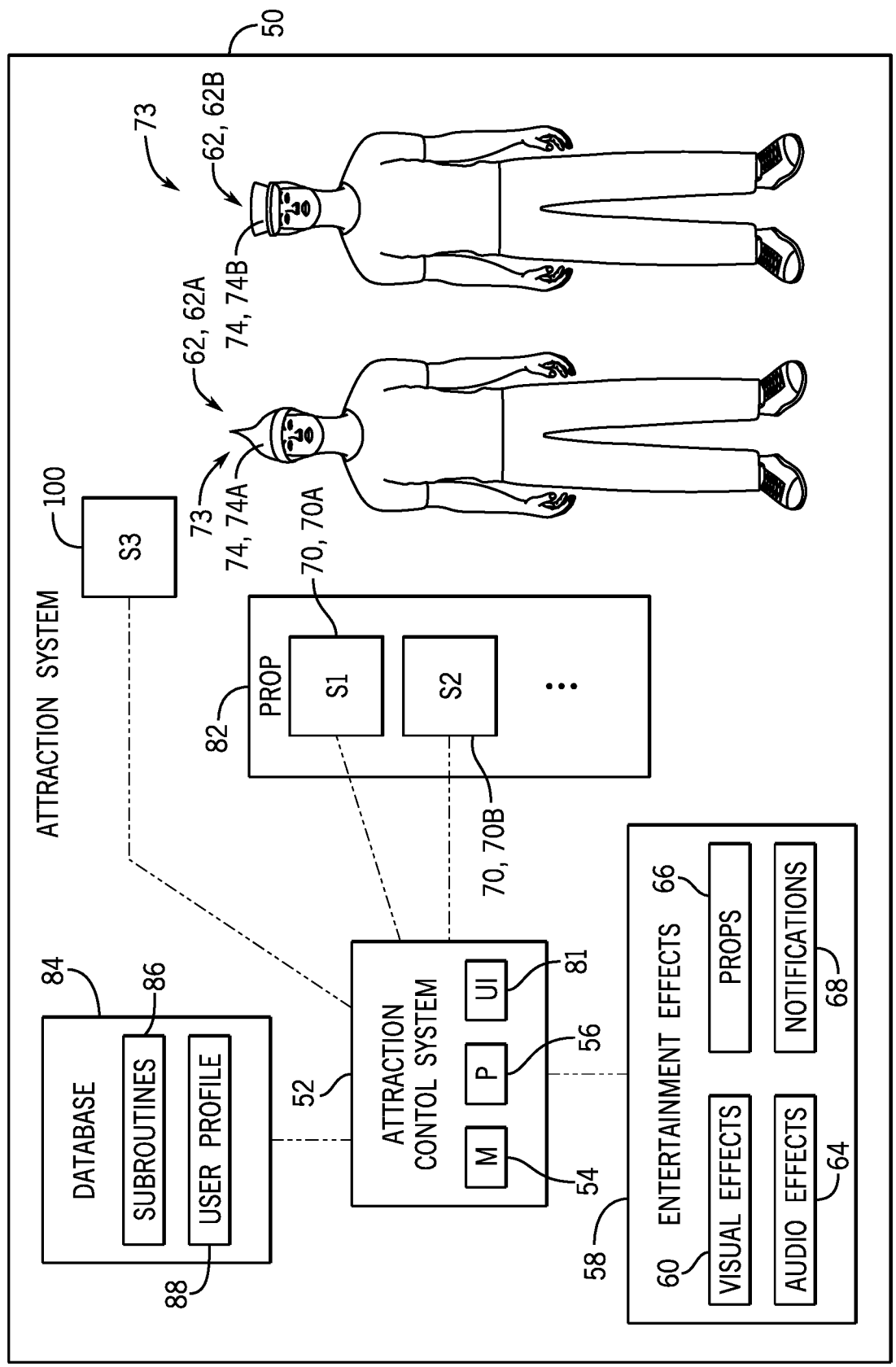
FIG. 2 is a schematic diagram of an embodiment of an attraction system having an adjustment control system configured to operate the attraction system based on data transmitted by a mmWave sensor, in accordance with an aspect of the present disclosure.

FIG. 2 is a schematic diagram of an embodiment of the attraction system 50 in which there is a first guest 62A and a second guest 62B within the attraction system 50. The attraction system 50 also includes the mmWave sensors 70, which may send respective signals that reflect off the guests 62 to enable the attraction control system 52 to determine various parameters associated with the guests 62. The mmWave sensors 70 may also transmit data indicative of such parameters to the attraction control system 52 to cause the attraction control system 52 to operate the attraction system 50 based on the parameters. As an example, the data transmitted by the mmWave sensors 70 may indicate that there are two guests 62, and the attraction control system 52 may therefore operate the entertainment effects 58 accordingly, such as to present a narrative that is directed to two guests 62 instead of a narrative that is directed to a single guest 62 or to more than two guests 62. For instance, the attraction control system 52 may select a subroutine from the database 84 based on the determination that there are two guests 62 in the attraction system 50. The attraction control system 52 may coordinate with the mmWave sensors 70 to identify skeletal structures of the guests 62 to facilitate not only detection of a number of guests but also their physical movements within the attraction system 50. By focusing the mmWave sensors 70 on body structure, interference from clothing (e.g., a long jacket or dress) can be limited to focus computing functions more efficiently on bodily movement, which may facilitate gameplay or other interactive aspects of the attraction system 50.

Additionally or alternatively, the attraction control system 52 may operate the attraction system 50 based on respective parameters (e.g., physical profiles) uniquely associated with the guests 62. For example, during a first operation of the attraction system 50 in which the first guest 62A is in the attraction system 50, the mmWave sensors 70 may detect a first set of parameters associated with the first guest 62A, and the attraction control system 52 may operate the attraction system 50 in accordance with a first subroutine (e.g., based on the first set of parameters, based on a user input). The attraction control system 52 may also store a first user profile 88 that associates the first operational settings with the first set of parameters associated with the first guest 62A. During a second operation of the attraction system 50 in which the second guest 62B is in the attraction system 50, the mmWave sensors 70 may detect a second set of parameters associated with the second guest 62B, and the attraction control system 52 may operate the attraction system 50 in accordance with a second subroutine (e.g., based on the second set of parameters, based on user input). The attraction control system 52 may also store a second user profile 88 that associates the second operational settings with the first set of parameters associated with the second guest 62B. During a third operation in which both the first guest 62A and the second guest 62B are in the attraction system 50, the mmWave sensors 70 may detect both the first and second set of parameters, and the attraction control system 52 may therefore determine that both the first guest 62A and the second guest 62B are in the attraction system 50 based on the association between the first and second set of parameters with the first and second user profiles 88, respectively. The attraction control system 52 may therefore operate the attraction system 50 in accordance with both the first and the second subroutines associated with the first and second user profiles 88, respectively.

In a further embodiment, the attraction control system 52 may determine costuming 73 (e.g., regular or themed clothing and/or accessories) associated with each of the guests 62. In the illustrated attraction system 50, the first guest 62A is associated with (e.g., wearing) a first headwear 74A, and the second guest 62B is associated with (e.g., wearing) a second headwear 74B. Each headwear 74 may be associated with a respective subroutine. For example, the first headwear 74 may be associated with a nautical narrative, and the second headwear 74B may be associated with an aerial narrative. Thus, based on a determination that the guests 62 are respectively wearing the first headwear 74A and the second headwear 74B, the attraction control system 52 may operate each of the associated subroutines, such as both the nautical narrative and the aerial narrative. Additionally or alternatively, the attraction control system 52 may operate a single subroutine that is associated with a combination of the first headwear 74A and the second headwear 74B instead of operating two separate subroutines. In any case, the attraction control system 52 may operate the attraction system 50 based on respective parameters associated with multiple guests 62. For example, instead of the headwear 74, any of various other costuming 73 (e.g., an eyepatch, a toy sword) or physical attributes (e.g., facial features) may be detected and utilized to guide the attraction control system 52 to provide a particular narrative. Indeed, using a matrix of the mmWave sensors 70 or controlling one or more of the mmWave sensors 70 to operates across a range of signal types, layers of data can be obtained and used by the attraction control system 52 to provide entertainment (e.g., narrative changes). For example, multiple layers of costuming 73 and/or combinations of layers of costuming 73 (e.g., a coat, a shirt under the coat, and a necklace under the shirt) can be detected and utilized by the attraction control system 52 to make more granular decisions about the effects to provide. As a specific example, a particular jacket in combination with a particular piece of jewelry may be associated with a different effect than the same jacket with a different piece of jewelry.

It should be noted that the mmWave sensors 70 may be used in combination with another sensor 100 to facilitate determination of an identification of the guests 62. For example, the sensor 100 may include an audio sensor and/or another visual sensor, such as an infrared sensor, a camera, or a light detection and ranging sensor. Indeed, the attraction control system 52 may receive multiple data from different sensors to identify guests 62. That is, the combination of the mmWave sensors 70 and the sensor 100 may detect data that is uniquely associated with respective guests 62 to enable the attraction control system 52 to distinguish guests 62 from one another.

In one embodiment, the attraction control system 52 may operate the attraction system 50 in accordance with identified guests 62 based on a confidence value indicative of an estimated accuracy in which the guests 62 have been accurately identified via data received from the mmWave sensors 70 and/or the sensor 100, such as based on an association with a user profile 88. For example, the attraction control system 52 may operate the attraction system 50 in accordance with one or more subroutines associated with the user profile 88 in response to the confidence value being greater than a threshold confidence value. However, the attraction control system may operate the attraction system 50 in accordance with one or more other (e.g., default) subroutines that are not specifically associated with the user profile 88 in response to the confidence value being less than the threshold confidence value.

In an embodiment, the attraction control system 52 may use machine learning (e.g., supervised machine learning, unsupervised machine learning) in order to identify a target operation more accurately. As used herein, machine learning refers to algorithms and statistical models that the attraction control system 52 may use to perform a specific task without using explicit instructions, relying instead on patterns and inference. In particular, machine learning generates a mathematical model based on data (e.g., sample or training data, historical data) in order to make predictions or decisions without being explicitly programmed to perform the task. In this way, as subsequent operations are implemented (e.g., based on identified guests 62, identified biometric data, identified costuming 73), stored information that associates received data (e.g., from the mmWave sensors 70, from the sensor 100) with target operations may be updated to more accurately reflect the target operation of the attraction system 50. That is, the attraction control system 52 may use machine learning for dynamically updating the information used to determine the target operation of the attraction system 50, such as based on a machine learning model. As such, the attraction control system 52 may operate the attraction system 50 more accurately to provide the desired experience to the guests 62.

Figure 3:
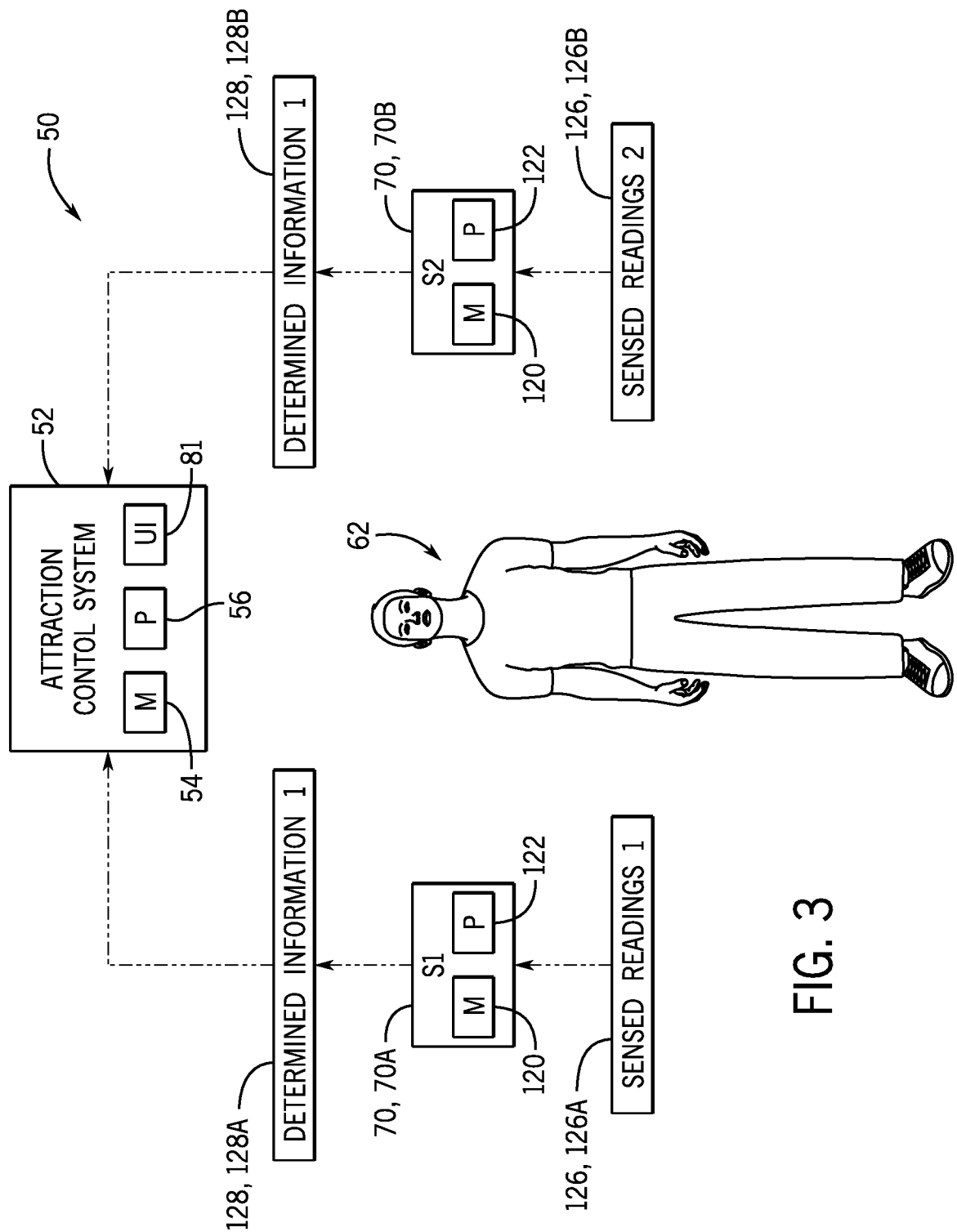
FIG. 3 is a schematic diagram of an embodiment of an attraction system having an attraction control system configured to utilize edge computing to adjust operation of the attraction system, in accordance with an aspect of the present disclosure.

FIG. 3 is a schematic diagram of an embodiment of the attraction system 50 in which edge computing is used to enable the attraction control system 52 to operate the attraction system 50 based on data transmitted by the mmWave sensors 70. Edge computing includes processing readings at local points (e.g., based on transmitted and reflected signals), such as via onboard equipment of the mmWave sensors 70, rather than at centralized or offloaded points, such as via the attraction control system 52 or via an external server. For example, each of the mmWave sensors 70 may include a respective memory 120 and processing circuitry 122, such as a respective control system that includes the memory 120 and the processing circuitry 122. The processing circuitry 122 of each mmWave sensor 70 may execute instructions stored in the corresponding memory 120 to process sensed readings 126, such as to directly identify the guest 62, to identify the costuming associated with the guest 62, to identify biometric data associated with the guest 62, to identify a target operation of the attraction system 50, or any combination thereof. To this end, each mmWave sensor 70 may be pre-heated or pre-loaded with certain information that may be useful for processing sensed readings 126. Additionally or alternatively, each mmWave sensor 70 may be communicatively coupled to storage (e.g., the database 84) and may reference information stored in the storage to process the sensed readings 126. In any case, each mmWave sensor 70 may access and use information to directly process the sensed readings 126.

After processing the sensed readings 126 to determine information 128 associated with the attraction system 50, such as an identification of the guest 62, costuming (e.g., clothing and/or an accessory) associated with the guest 62, biometric data associated with the guest 62, a target operation of the attraction system 50, or any combination thereof, the mmWave sensors 70 may transmit the determined information 128 to the attraction control system 52. As such, the attraction control system 52 may operate the attraction system 50 based on the determined information 128 received from the mmWave sensors 70 without having to process the sensed readings 126. That is, the attraction control system 52 may directly determine a target operation of the attraction system 50 without having to perform additional analysis of the sensed readings 126. In this manner, edge computing may facilitate a more rapid response for operating the attraction system 50 based on the sensed readings 126. Indeed, edge computing may be used in conjunction with machine learning, for example, in order to facilitate the target operation of the attraction system 50 to be quickly and accurately determined. For instance, in addition to accelerating data processing for general computations, thereby increasing the speed of adjusting the operation of the attraction control system 52, edge computing may further increase the speed of machine learning to determine subsequent target operations of the attraction control system 52 by using dedicated deep learning processing hardware.

In an embodiment, the attraction control system 52 may compare determined information 128 received from different mmWave sensors 70 to determine the target operation of the attraction system 50. For instance, the first sensor 70A may detect and process first sensed readings 126A to output first determined information 128A to the attraction control system 52. The second sensor 70B may detect and process second sensed readings 126B to output second determined information 128B to the attraction control system 52. The attraction control system 52 may compare the first determined information 128A with the second determined information 128B to operate the attraction system 50 accordingly. By way of example, in response to determining the first determined information 128A matches with the second determined information 128B (e.g., both mmWave sensors 70 identified the same guest 62), the attraction control system 52 may operate the attraction system 50 in accordance with a first subroutine (e.g., a subroutine associated with the guest 62). However, in response to determining the first determined information 128A (e.g., a first identity of the guest 62) does not match with the second determined information 128B (e.g., a second identify of the guest 62), the attraction control system 52 may operate the attraction system 50 in accordance with a second subroutine (e.g., a default subroutine that is not associated with the guest 62). Indeed, edge computing may be used to facilitate the attraction control system 52 to operate the attraction system 50 based on any of the techniques described above.

Figure 4:
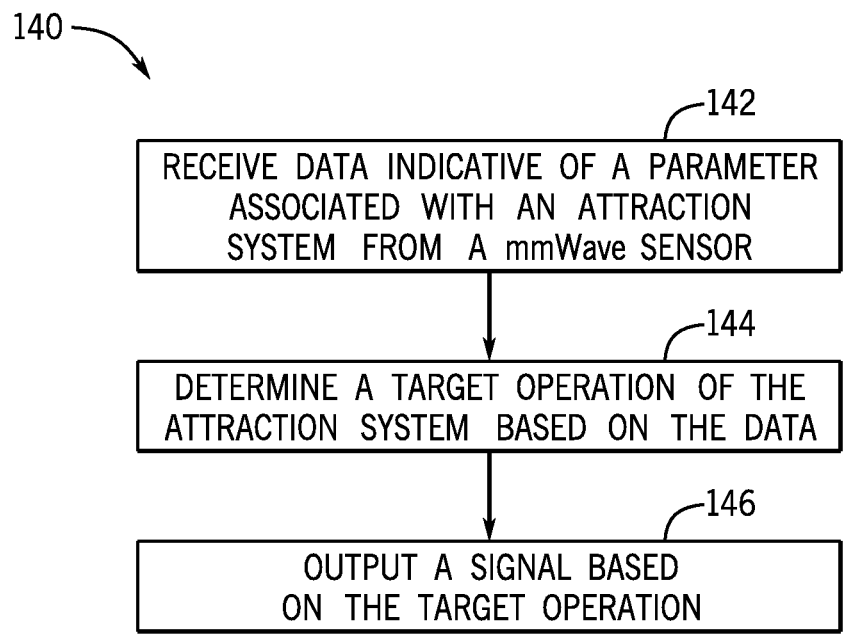
FIG. 4 is a flowchart of an embodiment of a method or process for operating an attraction system based on data transmitted by a mmWave sensor, in accordance with an aspect of the present disclosure.

FIG. 4 is a flowchart of an embodiment of a method or process 140 for operating an attraction system based on data received from a mmWave sensor. As an example, the method 140 may be performed by one or more processors, such as the processing circuitry 56 of the attraction control system 52, the processing circuitry 122 of the mmWave sensor 70, or both. It should be noted that certain steps of the method 140 may be performed differently in different embodiments. For instance, additional steps may be performed, and/or certain steps may be removed, modified, and/or performed in a different order.

At block 142, data indicative of a parameter associated with the attraction system, such as with a guest of the attraction system, is received. In an embodiment, the data may include readings taken by the mmWave sensor and other sensors (e.g., a facial recognition camera). In an additional or alternative embodiment, the data may include data processed by the mmWave sensor. In any case, the data may be indicative of an identification of a guest, clothing and/or accessories associated with the guest, biometric data associated with the guest, or any combination thereof.

At block 144, a determination may be made regarding a target operation of the attraction system based on the data. That is, the target operation of the attraction system may be based on the parameter associated with the guest to provide a desirable experience for the guest. For example, the target operation may include a target operation of various entertainment effects provided during operation of the attraction system based on a layering of data detected by one or more mmWave sensors (e.g., a matrix of mmWave sensors or a single mmWave sensor operating across a spectrum of signal types) operating at different wavelengths to detect physical features associated with a guest at different physical layers (e.g., a coat, a shirt, a wristband). At block 146, after a determination has been made regarding the target operation of the attraction system, a signal is output based on the determined target operation so as to adjust the operation of the attraction system toward the target operation.

In an embodiment, the method 140 may be used to adjust the operation of the attraction system to elicit or induce a particular response from the guest. For instance, it may be desirable to provide the guest with a particular excitement level. The excitement level may be associated with a target range of biometric data values, such as a target range of heart rates and/or a target range of respiratory rates, which may be determined based on experimental operations and/or calibrated data. Thus, if the biometric data is indicative that the attraction system is providing too much excitement (e.g., the biometric data exceeds the target range of heart rates, the biometric data exceeds the target range of respiratory rates), the signal may be output to adjust the operation of the attraction system to reduce an intensity of the experience provided to the guest to avoid over-exciting the guest. However, if the biometric data (e.g., a pulse rate detected by a mmWave sensor) is indicative that the attraction system is not providing enough excitement (e.g., the biometric data is below the target range of heart rates, the biometric data is below the target range of respiratory rates), the signal may be output to adjust the operation of the attraction system to increase the intensity of experience provided to the guest. In one embodiment, the excitement level, and therefore the target range of biometric data values, may be set based on a user input. By way of example, the guest may select a desirable excitement level to be provided by the attraction system. Therefore, the operation of the attraction system may be adjusted to align with the experience desired by the guest.

In an additional or alternative embodiment, the data may be used to determine an identification of the guest, such as a user profile associated with the guest, and to operate the attraction system based on the identification of the guest. By way of example, the data may include a physical profile uniquely associated with the guest. The identification or user profile of the guest may also be associated with a target operation of the attraction system, such as a previous operation of the attraction system to entertain the guest, a preferred operation set by the guest (e.g., via a user input), and the like. Therefore, upon identification of the guest based on the data, the signal may be output to adjust the operation of the attraction system based on the target operation associated with the guest.

In a further embodiment, the data may be indicative of costuming (e.g., clothing and/or an accessory) associated with the guest, such as a clothing and/or an accessory selected from a collection of possible clothing and/or accessories. Indeed, each costuming may be associated with a target operation of the attraction system and/or a combination of costuming may be associated with a target operation of the attraction system. For instance, the experience provided by the attraction system may align with a theme associated with the costuming to provide a more immersive experience for the guest. In any case, upon identification of the costuming based on the data, the signal may be output to adjust the operation of the attraction system based on the target operation associated with the particular costuming.

In any case, it should be noted that the data may be used to adjust any suitable operation of the attraction system to control the entertainment provided to a guest in the attraction system. For instance, the signal may be output to control operation of entertainment effects, including visual effects, audio effects, props, and/or notifications. The operation of the entertainment effects may provide a desirable experience to the guest.

While only certain features of embodiments of the present disclosure have been illustrated and described herein, many modifications and changes will occur to those skilled in the art. It is, therefore, to be understood that the appended claims are intended to cover all such modifications and changes as fall within the true spirit of the present disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. An attraction system for entertaining guests, the attraction system comprising:
a millimeter wave (mmWave) sensor configured to:
transmit a signal within the attraction system and to receive a reflection of the signal; and detect costuming based on the reflection of the signal;
a control system communicatively coupled to the mmWave sensor, wherein the mmWave sensor is configured to transmit data to the control system based on the reflection of the signal, wherein the data is indicative of the costuming, and the control system is configured to perform operations comprising:
determining a target operation of the attraction system based on the data received from the mmWave sensor indicative of the costuming; and
operating the attraction system based on the target operation.

2. The attraction system of claim 1, wherein the control system is configured to perform operations comprising:
identifying biometric data associated with a guest based on the data received from the mmWave sensor;
comparing the biometric data with a range of biometric data values; and
operating the attraction system based on the comparison between the biometric data and the range of biometric data values.

3. The attraction system of claim 2, wherein the biometric data comprises a heart rate of the guest, a respiratory rate of the guest, or both.

4. The attraction system of claim 1, comprising a matrix of mmWave sensors that includes the mmWave sensor, wherein the matrix of mmWave sensors is configured to detect the costuming by detecting different combinations of a plurality of costuming layers via a cascading of signals to provide the data, wherein the control system is configured to determine one or more target operations based on the different combinations of the plurality of costuming layers.

5. The attraction system of claim 1, wherein the control system is configured to perform operations comprising identifying a user profile associated with a guest based on the data received from the mmWave sensor, wherein the user profile comprises stored data indicative of the target operation of the attraction system.

6. The attraction system of claim 5, wherein the stored data comprises a physical profile associated with the guest.

7. The attraction system of claim 1, wherein the signal comprises a frequency that is between 60 and 90 gigahertz.

8. The attraction system of claim 1, comprising a cascade of mmWave sensors that comprises the mmWave sensor.

9. A tangible, non-transitory, computer-readable medium comprising executable instructions, wherein the instructions, when executed by processing circuitry, are configured to cause the processing circuitry to perform operations for an attraction system, the operations comprising:
receiving data from a millimeter wave (mmWave) sensor, wherein the data is indicative of a parameter associated with a guest within the attraction system;
identifying a user profile associated with the guest based on the data received from the mmWave sensor, wherein the user profile comprises stored data associated with the guest from a previous interaction with the attraction system;
determining a target operation of the attraction system based on the stored data associated with the user profile; and
operating the attraction system based on the target operation.

10. The tangible, non-transitory, computer-readable medium of claim 9, wherein the instructions, when executed by the processing circuitry, are configured to cause the processing circuitry to perform operations comprising:
receiving first data from the mmWave sensor at a first time;
associating the first data with the user profile stored in a database;
operating the attraction system in accordance with a subroutine; and
associating the subroutine with the user profile.

11. The tangible, non-transitory, computer-readable medium of claim 10, wherein the instructions, when executed by the processing circuitry, are configured to cause the processing circuitry to perform operations comprising:
receiving second data from the mmWave sensor at a second time;
comparing the second data with the first data associated with the user profile;
determining the second data matches with the first data; and
operating the attraction system in accordance with the subroutine associated with the user profile in response to determining the second data matches with the first data.

12. The tangible, non-transitory, computer-readable medium of claim 10, wherein the instructions, when executed by the processing circuitry, are configured to cause the processing circuitry to perform operations comprising:
receiving a user input indicative of an operation of the attraction system; and
operating the attraction system in accordance to the subroutine based on the user input.

13. The tangible, non-transitory, computer-readable medium of claim 9, wherein the data is indicative of a type of media viewer being used by the guest of the attraction system, and the instructions, when executed by the processing circuitry, are configured to cause the processing circuitry to perform operations comprising providing media corresponding to the type of media viewer.

14. The tangible, non-transitory, computer-readable medium of claim 9, wherein the data is indicative of costuming associated with the guest, and the instructions, when executed by the processing circuitry, are configured to cause the processing circuitry to perform operations comprising operating the attraction system in accordance with a subroutine associated with the costuming in response to receiving the data.

15. The tangible, non-transitory, computer-readable medium of claim 14, wherein the data is indicative of a first layer of the costuming and a second layer of the costuming, the subroutine is a first subroutine associated with the first layer of the costuming, and the instructions, when executed by the processing circuitry, are configured to perform operations comprising operating the attraction system in accordance with the first subroutine associated with the first layer of costuming and in accordance with a second subroutine associated with the second layer of costuming in response to receiving the data.

16. The tangible, non-transitory, computer-readable medium of claim 9, wherein the instructions, when executed by the processing circuitry, are configured to cause the processing circuitry to perform operations comprising sending a notification to a mobile device based on the data, wherein the notification includes a narration corresponding to the target operation of the attraction system.

17. An attraction system for entertaining a guest, the attraction system comprising:
a first millimeter wave (mmWave) sensor configured to transmit a first signal within the attraction system and to receive a reflection of the first signal;

a second mmWave sensor configured to transmit a second signal within the attraction system and to receive a reflection of the second signal; and a control system communicatively coupled to the first mmWave sensor and to the second mmWave sensor, wherein the first mmWave sensor is configured to transmit first data to the control system based on the reflection of the first signal, the second mmWave sensor is configured to transmit second data based on the reflection of the second signal, and the control system is configured to perform operations comprising:
  determining a target operation of the attraction system based on the first data, the second data, or both;
  operating the attraction system based on the target operation; and
  sending a notification to a mobile device based on the first data, the second data, or both.

18. The attraction system of claim 17, comprising a first plurality of mmWave sensors that comprises the first mmWave sensor and comprising a second plurality of mmWave sensors that comprises the second mmWave sensor, wherein the respective first signals transmitted by each mmWave sensor of the first plurality of mmWave sensors comprise a first frequency that is between 60 and 90 gigahertz, the respective second signals transmitted by each mmWave sensor of the second plurality of mmWave sensors comprise a second frequency that is greater than 90 gigahertz, and the control system is configured to operate the first plurality of mmWave sensors, the second plurality of mmWave sensors, or both, to adjust the first frequency, the second frequency, or both, based on the target operation.

19. The attraction system of claim 17, comprising a prop, wherein the first mmWave sensor, the second mmWave sensor, or both, are embedded within the prop.

20. The attraction system of claim 17, wherein the control system is configured to perform operations comprising controlling a visual effect, an audio effect, a prop, a notification, or any combination thereof, based on the target operation.

* * * * *